United States Patent [19]
Hough et al.

[11] Patent Number: 4,776,322
[45] Date of Patent: * Oct. 11, 1988

[54] IMPLANTABLE ELECTROMAGNETIC MIDDLE-EAR BONE-CONDUCTION HEARING AID DEVICE

[75] Inventors: Jack V. D. Hough, Yukon; Kenneth J. Dormer, Edmond, both of Okla.; Kenneth E. Barton, Jr.; Robert Y. Chow, both of Jacksonville, Fla.

[73] Assignee: Xomed, Inc., Jacksonville, Fla.

[ * ] Notice: The portion of the term of this patent subsequent to Aug. 12, 2003 has been disclaimed.

[21] Appl. No.: 898,050

[22] Filed: Aug. 18, 1986

Related U.S. Application Data

[63] Continuation-in-part of Ser. No. 736,766, May 22, 1985, Pat. No. 4,606,329.

[51] Int. Cl.$^4$ ............................................. H04R 25/00
[52] U.S. Cl. .................................... 128/1.6; 381/68.3; 381/68.6; 128/420.6
[58] Field of Search ................ 128/1 R, 1.6, 421, 423, 128/420.5, 420.6, 789; 381/68.3, 68.6

[56] References Cited

U.S. PATENT DOCUMENTS

| | | |
|---|---|---|
| 2,402,392 | 6/1946 | Goldschmidt . |
| 3,209,081 | 9/1965 | Ducote et al. . |
| 3,764,748 | 10/1973 | Branch et al. . |
| 3,870,832 | 3/1975 | Fredrickson . |
| 3,882,285 | 5/1975 | Nunley et al. ............... 179/107 E |
| 4,150,262 | 4/1979 | Ono ............................. 179/107 BC |
| 4,284,856 | 8/1981 | Hochmair et al. . |
| 4,352,960 | 10/1982 | Dormer et al. . |
| 4,419,995 | 12/1983 | Hochmair et al. . |
| 4,498,461 | 2/1985 | Hakansson . |

OTHER PUBLICATIONS

Scand Audiol 13; Mar. 1984; "Hearing Thresholds with Direct Bone Conduction Versus Conventional Bone Conduction"; by B. Hakansson, A. Tjellstrom and U. Rosenhall.

"Direct Bone Anchorage of External Hearing Aids", by A. Tjellstrom, J. Lindstrom, O. Hallen, T. Albrektsson and P. J. Bronemark; J. Biomed Eng., vol. 5; Jan. 1983.

"Bone Conduction Speech Discrimination"; by Mendell Robinson, MD and Stephen D. Kasden, MS; Arch Otolaryngol, vol. 103, Apr. 1977.

Primary Examiner—Edward M. Coven
Attorney, Agent, or Firm—Bell, Seltzer, Park & Gibson

[57] ABSTRACT

An implantable electromagnetic middle-ear bone-conduction hearing aid device is provided which is characterized by being carried entirely in the skull of the user, the absense of electrodes entering the middle-ear, and variability to meet a variety of pathological entities of the hearing impaired user. The device utilizes a sound processing component adapted to be positioned in the skull of the user and to extend from close proximity to the outside of the skull toward and within close proximity to the middle-ear of the user for receiving and converting sound into an electromagnetic signal and for transmitting the electromagnetic signal into the middle-ear of the user. A vibration generating component is adapted to be implanted in the small bones of the ossicular chain in the middle-ear for receiving the electromagnetic signal from the sound processing component and for vibrating the ossicular chain in response to such electromagnetic signal to stimulate the inner ear to create the perception of sound in the hearing impaired user.

14 Claims, 3 Drawing Sheets

U.S. Patent    Oct. 11, 1988    Sheet 3 of 3    4,776,322
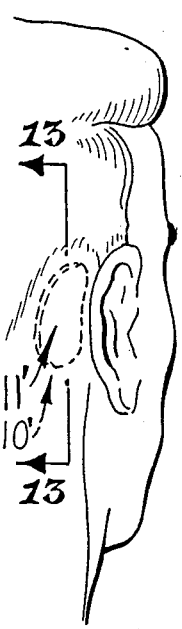
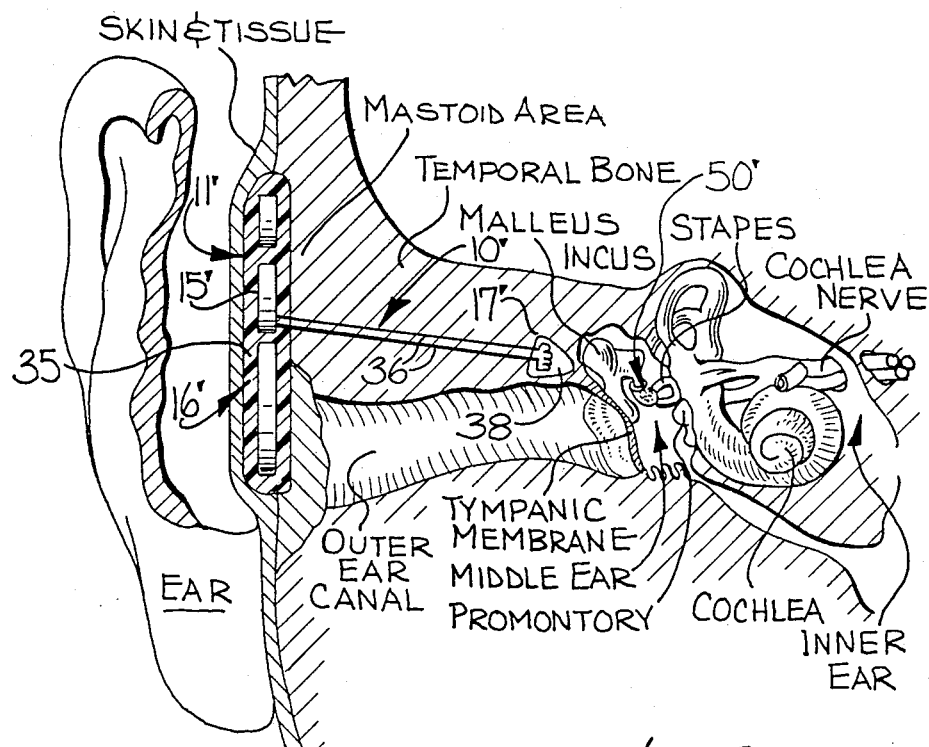
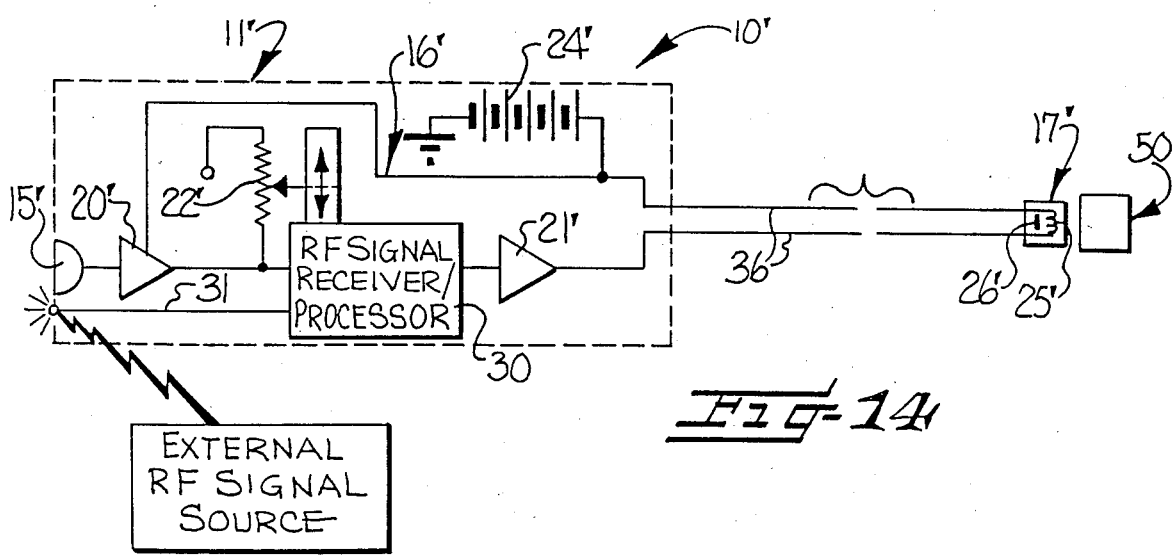

IMPLANTABLE ELECTROMAGNETIC MIDDLE-EAR BONE-CONDUCTION HEARING AID DEVICE

REFERENCE TO EARLIER FILED APPLICATION

This application is a continuation-in-part of and is filed under the provisions of 35 U.S.C. 120 from copending application Ser. No. 736,766, filed May 22, 1985, now U.S. Pat. No. 4,606,329, issued Aug. 19, 1986.

FIELD OF THE INVENTION

This invention relates to devices for aiding the hearing impaired and more particularly to an implantable electromagnetic middle-ear bone-conduction hearing aid device which stimulates the inner ear to create the perception of sound by conduction of vibrations through the small bones of the ossicular chain in the middle-ear of the user.

BACKGROUND OF THE INVENTION

The normal preception of sound occurs in a person when sound waves strike the tympanic membrane and cause it to vibrate. These vibrations are transmitted through the tiny bones of the ossicular chain in the middle-ear to the cochlea in the inner ear, which results in electrical impuses being transmitted through the auditory or cochlea nerve to the brain. Even if the sound conducting mechanisms of the middle-ear are functioning perfectly, a hearing loss can be experienced if the inner ear is damaged.

The more conventional hearing aid devices are of the "air conduction" type and are used to overcome a hearing loss due to inner ear damage (sensorineural loss) and/or hearing loss due to a mild impediment of the sound conducting mechanisms of the middle-ear. Such air conduction hearing aid devices work by simply amplifying the incoming sound and delivering the amplified sound signal by way of a speaker positioned in the outer ear canal. This amplified sound simply "overdrives" the ear's sound conducting mechanism. Since an air conduction hearing aid device must have some of its componentry in the outer ear canal, and since it also requires a fairly normal tympanic membrane and ossicular chain in the middle-ear, some hearing impaired persons are unable to derive any benefit from the air conduction hearing aid.

Persons who cannot benefit from an air conduction hearing aid can sometimes benefit from a "bone conduction" hearing aid. A bone conduction hearing aid works by converting the sound signal into a mechanical vibratory stimulus. Heretofore, the vibrating portion of most commercially-available hearing aids of this type has been placed against the skin, usually behind the ear, under some pressure. The vibrator transmits its vibrations through the skin and soft tissue into the bone structure of the skull. The vibration of the skull stimulates the cochlea and a sound is perceived. Such commercially available bone conduction hearing aid devices are not very popular due to several limitations. First, the devices are bulky and must be worn on a headband or a special eyeglass frame in order to keep the vibrator pressed tightly against the skull. In addition, because the vibration must be transmitted through the skin and soft tissue overlying the skull, the fidelity of sound and the efficiency of these types of hearing aid devices are poor.

Proposals have been made for improving bone conduction devices for stimulating the inner ear. One such proposal is disclosed in U.S. Pat. No. 3,209,081 in which a radio receiver is implanted underneath the skin and includes a vibration generating means which is connected to the temporal bone subcutaneously. A transmitter may be located at any remote place on the body of the user within the range of the implanted radio receiver for generating a modulated signal in response to sound received by a microphone. This modulated signal is received by the radio receiver and the vibrator is caused to vibrate in response to the modulated signal and set up vibrations within the temporal bone which in turn stimulates the inner ear to create a preception of sound. This implanted radio receiver is quite complex and includes numerous implanted electronic components including a power supply, which are susceptible to malfunction and other potential problems which could cause extreme difficulty due to the implanted nature thereof.

Another proposal relates to some experimental work conducted in Europe and described in a published paper wherein a direct bone conduction hearing aid device was implanted which included a bone screw implanted directly in the temporal bone subcutaneously and a post connected directly thereto. This post extends percutaneously (through the skin) to a location externally of the skin. A vibrator which creates vibrations in response to a modulated signal is connected to this post and vibrations are transmitted by the post to the bone screw and thence to the temporal bone of the skull to stimulate the inner ear and create the preception of sound. This device has distinct disadvantages, not the least of which are the likelihood of infection and the undesirability of a ceramic element extending permanently through the skin from aesthetic, psychological and comfort standpoints.

To overcome the problems presented with the above previously-proposed bone conduction hearing aid devices, a development was made, as disclosed in co-pending U.S. application Ser. No. 737,188 of May 23, 1985, now U.S. Pat. No. 4,612,915 of Sept. 23, 1986, filed under the provisions of 35 U.S.C. 120 from Ser. No. 674,176 of Nov. 23, 1984 (now abandoned), and assigned to the assignee of the present application, in which a direct bone conduction hearing aid device is proposed where the signal transmitting device is held in place without unsightly or uncomfortable external devices. This bone conduction hearing aid device includes sound processing mechanism for converting sound into an analog electromagnetic signal and having an output transmitter for transmitting the electromagnetic signal and being adapted to be placed supercutaneously on the skull of a hearing impaired person and having a first magnetic means therein. The device further includes a vibration generating mechanism adapted to be implanted subcutaneously and secured to a skull bone of the hearing impaired person and having second magnetic means. This second magnetic means (1) cooperates with the first magnetic means to hold said transmitter in position supercutaneously on the skull of the hearing impaired person, (2) receives the electromagnetic signal from said transmitter of said sound processing means, and (3) vibrates the skull bone in response to such electromagnetic signal. With this device, vibrations are generated subcutaneously in response to the analog electromagnetic signal and conducted through the bones of the skull to stimulate the inner ear to create the perception of sound in the hearing impaired person.

While this development of the aforesaid co-pending patent application performed satisfactorily for many cases, there are situations in which direct vibrations of the ossicles of the middle-ear are more desirable and may provide a more enhanced perception of sound in the hearing impaired person.

For these latter described cases, there has been proposed in U.S. Pat. No. 3,870,832 an implantable middle-ear bone-conduction hearing aid device which utilizes a sound transducer means for converting audio signals to electric signals and electromagnetic transducer means for receiving the electrical signals and converting the electrical signals into mechanical movement of the stapes bone of the ossicular chain in the inner ear. The device of this patent includes a magnet that is permanently attached to the stapes of the ossicular chain in the inner ear, an electromagnetic coil implanted in the temporal bone of the user and extending through the skin to be attached to a sound processing means outside the skin. The electromagnetic transducer receives electrical signals and transmits them by way of electrodes extending therefrom and into the middle-ear of the user and attached to the magnet secured to the stapes of the ossicular chain in the middle-ear of the user.

While this device of U.S. Pat. No. 3,870,832 directly stimulates the ossicular chain of the inner ear of the user by bone conduction, it has many disadvantages and limitations including the following. The hearing aid device requires a percutaneous element extending through the soft tissue and skin of the user behind the ear which creates the likelihood of infection from permanently open skin and bacterial invasion. It is also unacceptable from cosmetic, psychological and comfort standpoints. Secondly, this patented device utilizes electrodes which extend directly into the middle-ear of the user and are very difficult to implant surgically and open up strong possibilities of electrode fractures, insulation leaks and current leaks. Thirdly, this device only provides for a vibration generating mechanism to be attached to the head of the stapes of the ossicular chain in the middle-ear. In many cases, the promontory is too high on the inferior side to allow attachment of a vibration generating mechanism to the head of the stapes. Also, there are occasions when the facial ridge impinges on the stapes and would make such application impractical. In summary, there are many cases in which attachment of a vibration generating means to the head of the stapes in the ossicular chain will not provide the desired stimulas to the inner ear to create the required perception of sound in the hearing impaired person.

To overcome these last discussed problems, the invention of the parent application, now U.S. Pat. No. 4,606,329, from which the present application was filed under the provisions of 35 U.S.C. 120, provides an implantable electromagnetic middle-ear bone-conduction hearing aid device which is characterized by the absence of electrodes entering the middle ear and variability to meet a variety of pathological entities of the hearing impaired user, while providing increased comfort and aesthetic appearance.

Such hearing aid device included a sound processing means for converting sound into an analog electromagnetic signal and an output transmitter adapted to be placed supercutaneously on the skull of the user for transmitting the electromagnetic signal transcutaneously. A signal receiving and transmitting means is adapted to be implanted subcutaneously in the bone of the user outside of the middle-ear for receiving the transcutaneous electromagnetic signal from the sound processing means transmitter and for transmitting the electromagnetic signal subcutaneously into the middle-ear of the user. Vibration generating means are adapted to be implanted in or on any of the small bones of the ossicular chain in the middle-ear for receiving the subcutaneous electromagnetic signal from the signal receiving and transmitting means and for vibrating the ossicular chain in the middle-ear in response to such electromagnetic signal to stimulate the inner ear to create the perception of sound in the hearing impaired user.

A preferred embodiment of such implantable electromagnetic middle-ear bone-conduction hearing aid device of this parent application discloses an electromagnetic signal receiving and transmitting means which includes electromagnetic signal receiving means attached subcutaneously to the mastoid area of the temporal bone of the user, electrodes connected at one end to the electromagnetic signal receiving means for subcutaneously conveying an electrical signal and an electromagnetic signal transmitting means connected to the other end of the electrodes and adapted to be implanted in the temporal bone of the user just outside the middle-ear for transmitting an electromagnetic signal subcutaneously into the middle-ear of the user. In accordance with this preferred embodiment, the sound processing means transmitter and the signal receiving and transmitting means include magnetic means for cooperating with each other to hold the sound processing means transmitter in position supercutaneously behind the ear of the user without a percutaneous extension of the device through the skin of the user.

Although this preferred embodiment and the various forms of vibration generating components provided significant improvements over the prior art, the disadvantage still existed that a sound processing means was required to be carried on the body of the user outside of the skull and either entirely or partially magnetically held supercutaneously on the skull of the user.

OBJECTS AND SUMMARY OF THE INVENTION

With the foregoing in mind, it is the object of the present invention to provide improved embodiments of the electromagnetic middle-ear bone-conduction hearing aid device disclosed in the parent co-pending application, now U.S. Pat. No. 4,606,329, wherein the external sound processing means is eliminated and the entire hearing aid device is adapted to be positioned in the skull of the user.

It has been found by the present invention that this object may be accomplished by providing an implantable electromagnetic middle-ear bone-conduction hearing aid device characterized by being carried entirely in the skull of the user, the absence of electrodes entering the middle-ear, and variability to meet a variety of pathological entities of the hearing impaired user, in which such device includes the following. Sound processing means is adapted to be positioned in the skull of the user and to extend from close proximity to the outside of the skull toward and within close proximity to the middle-ear of the user for receiving and converting sound into an electromagnetic signal and for transmitting the electromagnetic signal into the middle-ear of the user. Vibration generating means are adapted to be implanted in or on the small bones of the ossicular chain in the middle-ear for receiving the electro-magnetic signal from the sound processing means and for vibrating the ossicular chain in response to such electro-magnetic signal to stimulate the inner ear to create the perception of sound in the hearing impaired user.

In accordance with a first preferred embodiment of the invention of the present application, the sound processing means adapted to be positioned in the skull of the user comprises a body portion molded to fit within the outer ear canal to extend from the outer opening thereof toward and within close proximity to the middle-ear of the user and including means within the body portion for receiving and converting sound into an electromagnetic signal and for transmitting the electromagnetic signal into the middle-ear of the user for receipt by the vibration generating means implanted in the small bones of the ossicular chain in the middle-ear.

In accordance with a second preferred embodiment of the invention of the present application, the sound processing means adapted to be positioned in the skull of the user comprises means adapted to be implanted subcutaneously in the bone of the skull of the user and to extend from close proximity to the outside of the skull toward and within close proximity to the middle-ear of the user for receiving and converting sound into an electromagnetic signal and transmitting the electromagnetic signal into the middle-ear of the user. In this second embodiment, the sound processing means is preferably implanted in the temporal bone of the user outside of the middle-ear and includes a sensitive microphone implanted subcutaneously in the mastoid area of the temporal bone for receiving sound waves, electronic means connected to the microphone for converting the sound waves received into the electromagnetic signal, and an output transmitter connected to the electronic means and adapted to be implanted in the temporal bone just outside of the middle-ear for transmitting the electromagnetic signal.

With these two preferred embodiments, the first embodiment provides a sound processing means which can be easily removed from the outer ear canal of the user for readjusting or repairing the electronics. With the second embodiment, a totally implantable hearing aid device is provided which creates no aesthetic disadvantages to the user.

BRIEF DESCRIPTION OF THE DRAWINGS

Some of the features and advantages of this invention having been briefly stated, others will appear from the detailed description which follows, when taken in conjunction with the accompanying drawings, in which—

FIG. 12 is a partial perspective view of the user of the hearing aid device of this invention viewed from the rear of the skull and showing the use of a second embodiment of a hearing aid device in accordance with this invention;

FIG. 13 is an enlarged sectional view through the ear canal of the user with the second embodiment of hearing aid device of this invention in position and taken generally along the line 13—13 of FIG. 12; and FIG. 14 is a schematic circuit diagram of the second embodiment of hearing aid device of this invention illustrated in FIG. 13.

DETAILED DESCRIPTION OF ILLUSTRATED EMBODIMENTS

Figure 1:
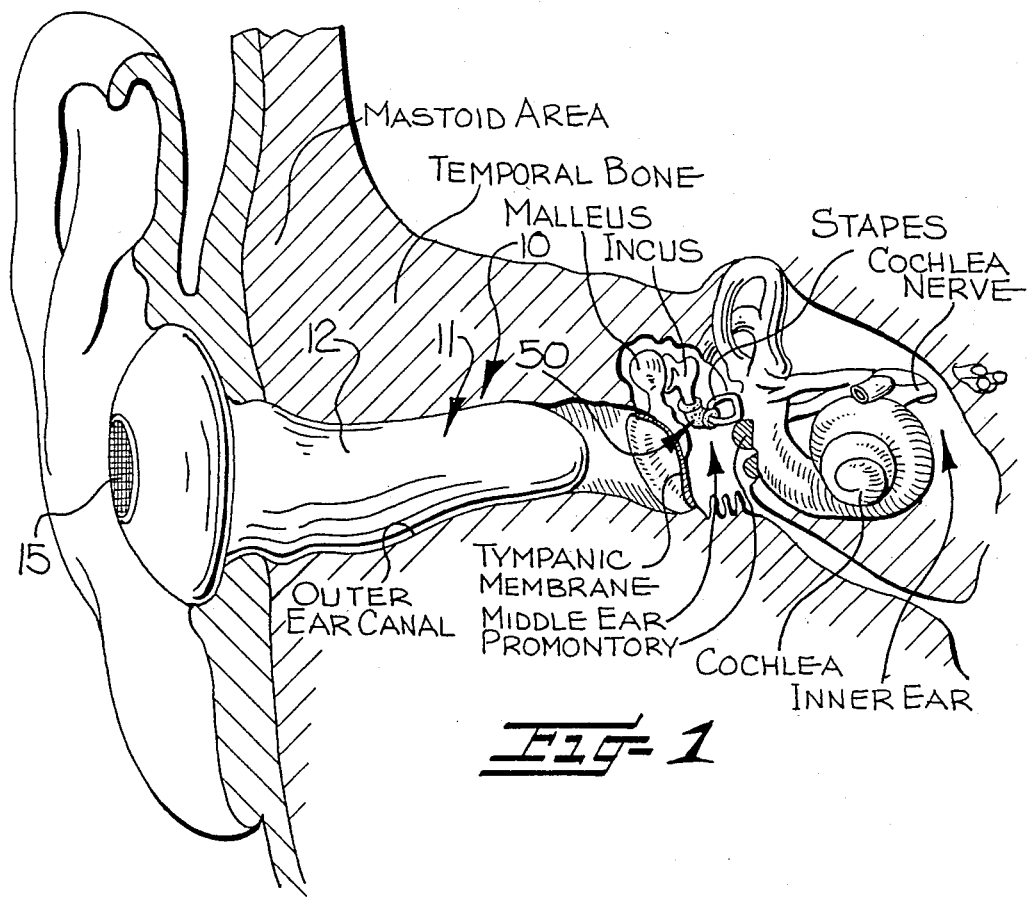
FIG. 1 is an enlarged sectional view through the ear canal of the user with the first embodiment of a hearing aid device in accordance with this invention in position.
Figure 2:
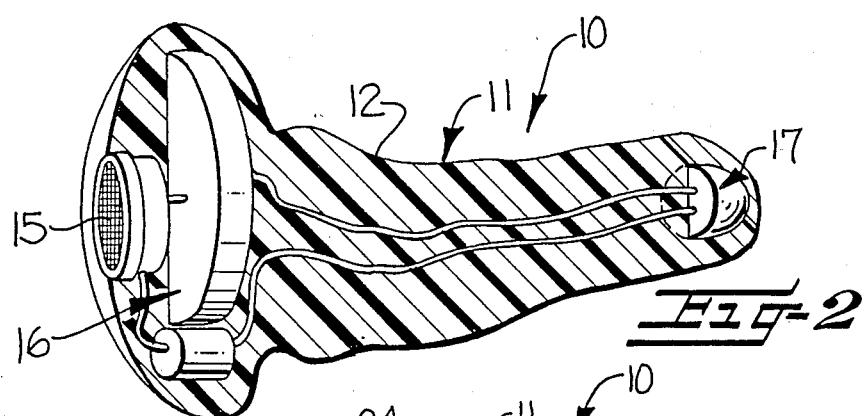
FIG. 2 is an enlarged, sectional view through the sound processing means utilized in the hearing aid device illustrated in FIG. 1.
Figure 3:
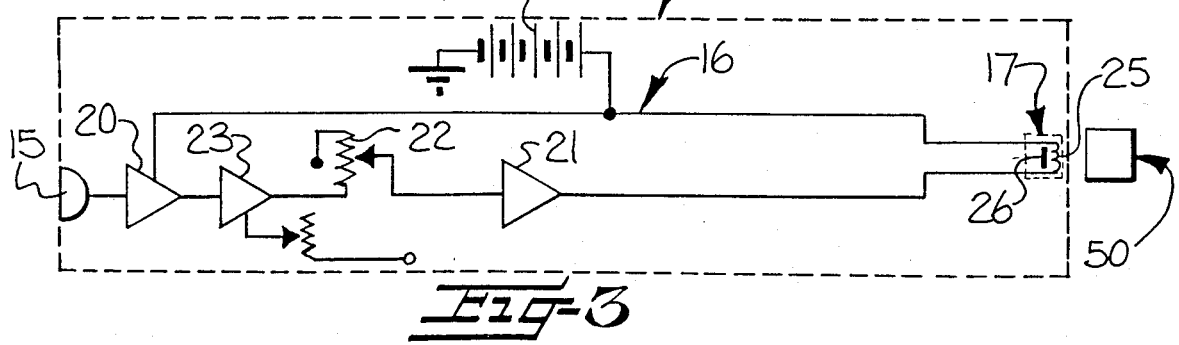
FIG. 3 is a schematic circuit diagram of the hearing aid device of FIG. 1.
Figure 4:
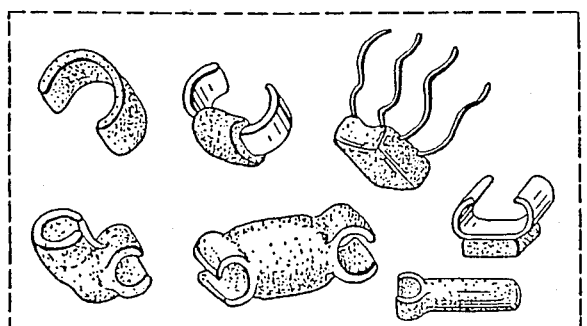
FIG. 4 is a composite view of various forms of the vibration generating component of the hearing aid device of this invention which may be implanted in any of the small bones of the ossicular chain the middle-ear of the user.

Referring now more specifically to the drawings, FIGS. 1–3 illustrate a first preferred embodiment of the implantable electromagnetic middle-ear bone-conduction hearing aid device in accordance with this invention and generally indicated at 10. FIGS. 12–14 illustrate a second preferred embodiment of the implantable electromagnetic middle-ear bone-conduction hearing aid device constructed in accordance with this invention and generally indicated at 10′ FIGS. 4–11 illustrate various forms of the vibration generating component or means 50 including some of the alternative variations of implanting this vibration generating component 50 into the small bones of the ossicular chain in the middle-ear of the hearing impaired person. However, it is to be understood that other arrangements are possible. The vibration generating component or means 50 and the various locations of implantation into the small bones of the ossicular chain of the middle-ear illustrated in FIGS. 4–11 are applicable for use with either the first embodiment of hearing aid device 10 of FIGS. 1–3 or the second embodiment of hearing aid device 10′ of FIGS. 12–14. In FIGS. 1 and 13, the entire ear canal of a user of the hearing aid device 10, 10′ along with other anatomical areas of the user are illustrated therein and have been appropriately labeled insofar as they pertain to the present invention.

Referring now to the first embodiment of hearing aid device 10 illustrated in FIGS. 1–3, there is included a sound processing means 11 adapted to be positioned in the skull of the user (FIG. 1) and to extend from close proximity to the outside of the skull toward and within close proximity to the middle-ear of the user for receiving and converting sound into an electromagnetic signal and for transmitting the electromagnetic signal into the middle-ear of the user.

The sound processing means 11 comprises a body portion 12 of suitable biocompatible material and molded to fit within the outer ear canal of the particular user to extend from the outer opening of the outer ear canal toward and within close proximity to the middle-ear of the user (FIG. 1). The sound processing means 11 further includes a sensitive microphone 15 for receiving sound waves, electronic means 16 connected to the microphone 15 for converting the sound waves received into the electromagnetic signal and an output transmitter 17 connected to the electronic means 16 for transmitting the electromagnetic signal. The sensitive microphone 15 includes a diaphram or membrane (not shown) which vibrates in response to the sound waves impinging thereon. The electrical signal from the microphone 15 is then amplified in the electronic means 16 by a preamplifier 20 and the amplified signal is fed to an output amplifier 21 through a volume control 22 and a tone frequency control 23 which provides a full or attenuated signal from the preamplifier 20 to the amplifier 21. A suitable battery or power source 24 is included in the electronic means 16. The output amplifier 21 amplifies the signal and then drives the output transmitter 17. The output transmitter 17 comprises an induction coil 25 wound about a core 26. The microphone 15 is positioned within the body portion 12 at the end thereof adapted to be positioned at the outer opening of the outer ear canal for receiving sound waves and the output transmitter 17 is positioned within the body portion 12 at the other end thereof adapted to be positioned with close proximity to the middle-ear and connected to the electronic means for transmitting the electromagnetic signal.

The hearing aid device 10 further includes the vibration generating means 50 which is adapted to be implanted in or on any of the small bones of the ossicular chain in the middle-ear of the user and includes magnetic means for receiving the electromagnetic signal from the output transmitter 17 of the sound processing means 11 and for vibrating the bones ossicular chain or a portion thereof in response to such electromagnetic signal to stimulate the normal functioning of the inner ear to create the perception of sound in the hearing impaired user.

This vibration generating means 50 is preferably in the form of a ceramic magnetic prosthesis formed of biocompatible material impregnated with rare earth magnetic particles. The vibration generating means 50 may take any desirable shape or form, such as the various forms illustrated in FIG. 4, and includes means for securement thereof to and between various small bones of the ossicular chain in the user depending upon anatomical variations. The vibration generating means 50 is not connected with any electrodes extending into the middle-ear of the user, thus avoiding the danger of leaks, shorts or breaking of electrodes and eliminating the very difficult task of surgically implanting the vibration generating component 50 while being attached to electrodes. Some of the alternative variations and arrangements of implanting this vibration generating component 50 into the small bones of the ossicular chain in the middle-ear of the hearing impaired person are illustrated in FIGS. 5–11 and will be described below. However, it is to be understood that other arrangements are possible.

Figure 5:
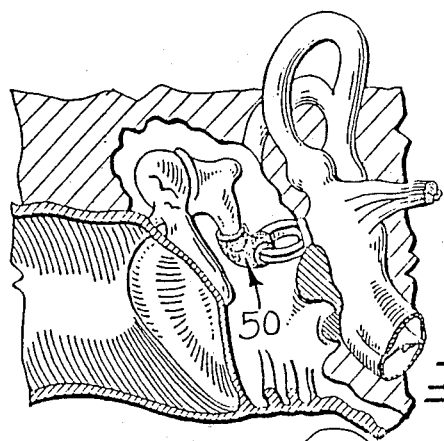
FIGS. 5–11 are partial views of the ear canal illustrating various alternative attachments of the vibration generating component in various locations in the ossicular chain of the middle-ear of the user.

Referring to FIG. 5, this is perhaps the most common arrangement envisioned. In this arrangement, the vibration generating means 50 is placed over the head of the stapes and under the long process of the incus in the ossicular chain in the middle-ear of the user. This arrangement provides a vibratory insert or prosthesis in the normal ossicular chain of the middle-ear of the user.

Figure 6:
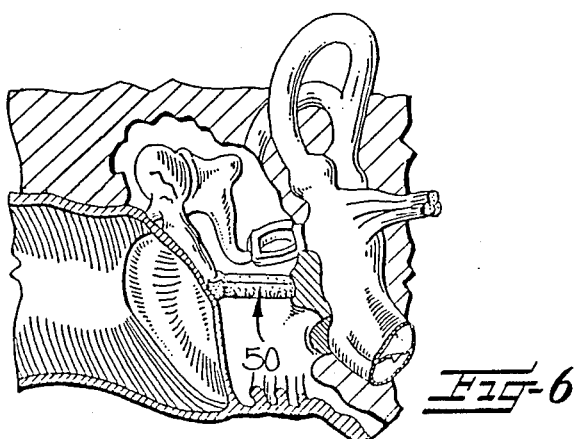

The arrangement of FIG. 6 illustrates the vibration generating means 50 secured between the promontory and the medial surface of the handle of the malleus under the tympanic membrane to provide natural vibrations of the ossicular chain duplicating the natural movement of the handle of the malleus when sound waves are imposed on the tympanic membrane of the user.

Figure 7:
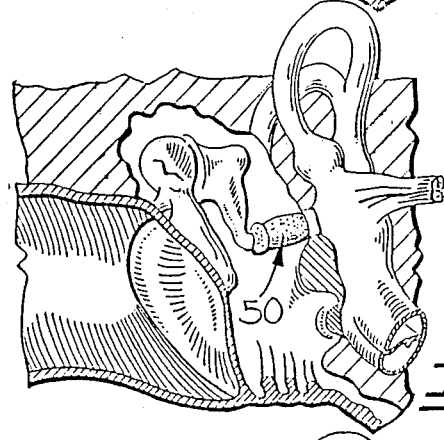

Referring next to FIG. 7, this arrangement shows the vibration generating means 50 secured between the foot plate of the stapes and the long process of the incus to function as a prosthesis when the superstructure of the stapes is missing in the user which may be caused by disease, injury or other processes.

Figure 8:
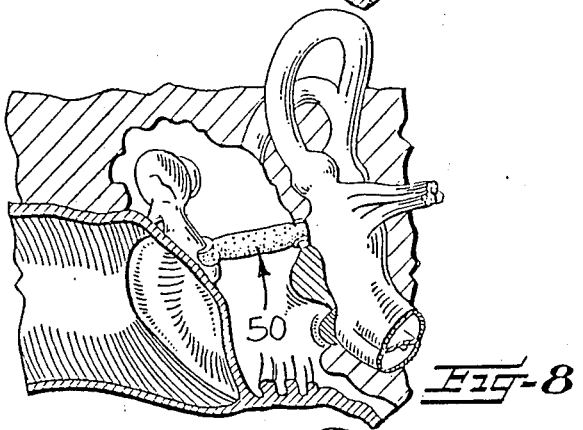

In FIG. 8, the vibration generating means 50 is shown secured between the handle of the malleus and the foot plate of the stapes to bypass the entire upper ossicular chain when the superstructure of the stapes has been damaged and the incus is no longer available for attachment in the user.

Figure 9:
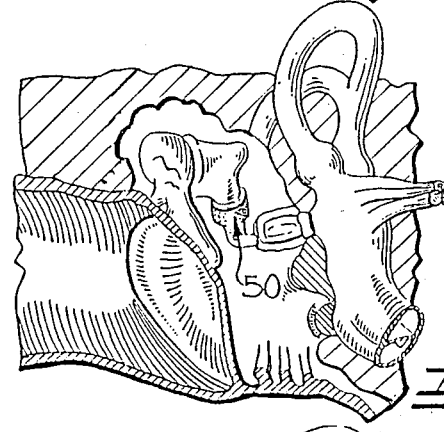

FIG. 9 illustrates the vibration generating means 50 secured to the long process of the incus which is possible in some anatomical situations, but not possible in others.

Figure 10:
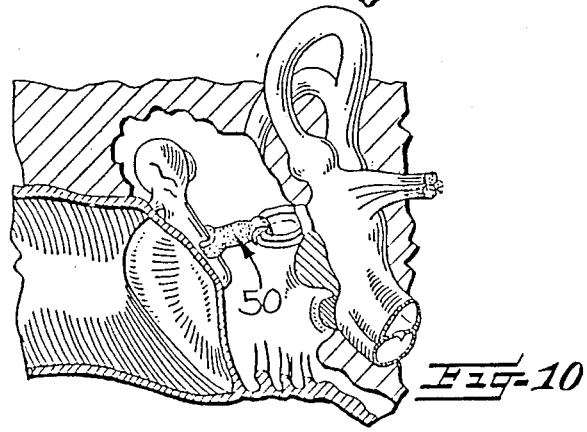

In FIG. 10, the vibration generating means 50 is attached between the head of the stapes and the handle of the malleus for use with ossicular chain defects producing a gap in the bridge from the tympanic membrane to the inner ear of the user. This application would be used when necrosis of the long process of the incus is present and produces a gap in the bridge from the tympanic membrane to the inner ear.

Figure 11:
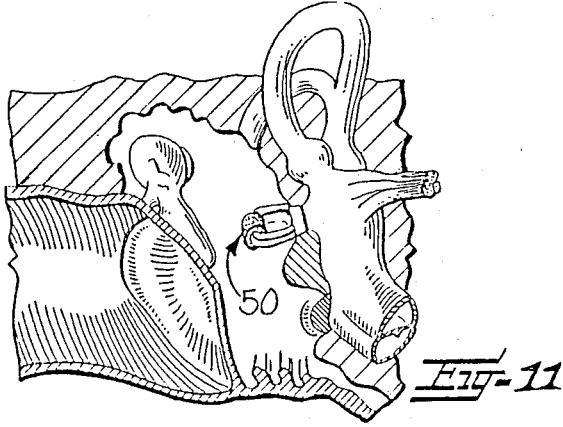

FIG. 11 illustrates the vibration generating means 50 attached to the head of the stapes in a situation similar to the application of FIG. 12, but without further attachment to the handle of the malleus, for simply vibrating the stapes when the bridge of the bones in the ossicular chain from the tympanic membrane to the inner ear contains a gap or has been disarticulated.

Referring now to the second embodiment of hearing aid device 10' illustrated in FIGS. 12–14, there is included a sound processing means 11' adapted to be positioned in the skull of the user (FIG. 13) and to extend from close proximity to the outside of the skull toward and within close proximity to the middle-ear of the user for receiving and converting sound into an electromagnetic signal and for transmitting the electromagnetic signal into the middle-ear of the user.

The sound processing means 11' is adapted to be implanted subcutaneously in the bone of the skull of the user and includes a sensitive microphone 15' adapted to be implanted subcutaneously in the mastoid area of the temporal bone for receiving sound waves (FIG. 13). Electronic means 16' are connected to the microphone 15' for converting the sound waves received into the electromagnetic signal. An output transmitter 17' is connected to the electronic means 16' for transmitting the electromagnetic signal into the inner ear of the user and is adapted to be implanted in the temporal bone just outside of the middle-ear (FIG. 13).

The sensitive microphone 15' includes a diaphram or membrane (not shown) which vibrates in response to the sound waves impinging thereon. The electrical signal from the microphone 15' is then amplified in the electronic means 16' by a preamplifier 20' and the amplified signal is fed to an output amplifier 21' through a volume control 22' which provides a full or attenuated signal from the preamplifier 20' to the amplifier 21'. A suitable battery or power source 24' is included in the electronic means 16'. The output amplifier 21' amplifies the signal and then drives the output transmitter 17'. The output transmitter 17' comprises an induction coil 25' wound about a core 26'.

The electronic means 16' further includes a radio frequency signal receiver/processor 30 positioned in the electronic means 16' between the preamplifier 20' and the amplifier 21' and includes a suitable antenna means 31 for receiving an external radio frequency signal to regulate and control the output perimeters of the electromagnetic signal produced by the electronic means 16' and transmitted by the output transmitter 17'. This radio frequency signal receiver/processor 30 is utilized in the event regulation of the implanted hearing aid device 10' is necessary for changed conditions of the hearing impaired user after the hearing aid device 10' is implanted within the user.

The microphone 15', electronic means 16' including battery 24', and other components described above may be contained within a biocompatible casing or housing 35 and are implanted just under the skin and tissue in the mastoid area of the temporal bone behind the outer ear of the user (FIG. 13). This housing or casing 35 may be suitably implanted in a cut-out or indentation in the mastoid area of the temporal bone just under the skin and tissue behind the outer ear of the user and may be adhesively or otherwise secured therein to prevent rotation or other movement thereof.

The electronic means 16 does include electrodes 36 extending from the housing or casing 35 in the mastoid area of the temporal bone through the temporal bone and to the output transmitter 17' which may also be encased in a housing of biocompatible material 38 and surgically implanted in the temporal bone just outside of the middle-ear (FIG. 13). The electrodes 36 and output transmitter 17' may be implanted by surgically boring a passageway from the indentation in the mastoid area of the temporal bone which contains the housing 35 and through the temporal bone. The electrodes 35 may also be covered with biocompatible material and the temporal bone may grow into contact with and surround the electrodes 36 and the output transmitter 17' for securing the same in place.

The hearing aid device 10' further includes a vibration generating means 50' adapted to be implanted in the small bones of the ossicular chain in the middle-ear for receiving the electromagnetic signal from the sound processing means 11' and for vibrating the ossicular chain in response to such electromagnetic signal to stimulate the inner ear to create the preception of sound in the hearing impaired user. The vibration generating means 50' utilized in this second embodiment of hearing aid device 10' may also take any of the desirable shapes or forms and may be implanted in any of the arrangements discussed above with respect to the first embodiment of hearing aid device 10, including those illustrated in FIGS. 4–11.

From the above description, it will be seen that the sound processing means 11 or 11' of the present invention is adapted to be positioned entirely outside of the middle ear of the user, and that the vibration generating means 50 or 50' is adapted to be implanted entirely in the middle ear of the user. By this arrangement, no wires or other components pass through the boundary of the middle ear. In this regard, the phrase "boundary of the middle ear" as used herein is intended to include the tympanic membrane and the other components which bound the cavity labelled "middle ear" in FIGS. 1 and 13.

In the drawing and specification, there have been disclosed preferred embodiments of the invention, and although specific terms are employed, they are used in a generic and descriptive sense only and not for purposes of limitation.

What is claimed is:

1. An electromagnetic middle ear hearing aid device characterized by the absence of any components passing through the boundary of the middle ear of the user and comprising sound processing means adapted to be positioned entirely outside of the middle ear of the user for receiving and converting sound into an electromagnetic signal and for transmitting the electromagnetic signal into the middle ear of the user, and an electromagnetic vibration generating means composed of magnetic material and adapted to be implanted entirely in the middle ear of the user and in contact with one or more of the small bones of the ossicular chain for receiving the electromagnetic signal from the sound processing means and for vibrating the ossicular chain in response to such electromagnetic signal to stimulate the inner ear to create the perception of sound in the user, whereby no components of said device pass through the boundary of the middle ear of the user.

2. The hearing aid device as defined in claim 1 wherein said sound processing means comprises a sensitive microphone for receiving sound waves, electronic means connected to said microphone for converting the sound waves received into the electromagnetic signal, and an output transmitter connected to said electronic means for transmitting the electromagnetic signal.

3. The hearing aid device as defined in claim 1 wherein said sound processing means comprises a body portion formed to fit within the outer ear canal and to extend from the outer opening thereof toward and within close proximity to the middle ear of the user, a sensitive microphone positioned within said body portion at the end thereof adapted to be positioned at the outer opening of the outer ear canal for receiving sound waves, electronic means positioned within said body portion and connected to said microphone for converting the sound waves received into the electromagnetic signal, and an output transmitter positioned within said body portion at the outer end thereof and adapted to be positioned within close proximity to the middle ear and connected to said electronic means for transmitting the electromagnetic signal.

4. The hearing aid device as defined in claim 1 wherein said sound processing means comprises a biocompatible casing adapted to be implanted under the skin in the mastoid area of the temporal bone behind the outer ear of the user, a sensitive microphone positioned within said casing for receiving sound waves, electronic means positioned within said casing and connected to said microphone for converting the sound waves received into the electromagnetic signal, and an output transmitter positioned outside of said casing and connected to said electronic means and adapted to be implanted in the temporal bone just outside the middle ear for transmitting the electromagnetic signal.

5. The hearing aid device as defined in claim 4 wherein said electronic means includes a radio frequency signal receiver and processor means for adjusting the electromagnetic signal produced.

6. The hearing aid device as defined in any one of claims 1, 2, 3, or 4 wherein said vibration generating means is configured as a prosthesis for replacing one or more of the bones of the ossicular chain.

7. The hearing aid device as defined in any one of claims 1, 2, 3, or 4 wherein said vibration generating means includes means for securing said vibrating generating means over the head of the stapes and under the long process of the incus providing a vibratory insert in the ossicular chain of the user.

8. The hearing aid device as defined in any one of claims 1, 2 ,3 or 4 wherein said vibration generating means inlcudes means for securing said vibration generating means between the promontory and the medial surface of the handle of the malleus under the tympanic membrane providing natural vibration of the ossicular chain duplicating the natural movement of the handle of the malleus when sound waves are imposed on the tympanic membrane of the user.

9. The hearing aid device as defined in any one of claims 1, 2, 3, or 4 wherein said vibration generating means includes means for securing said vibration generating means between the footplate of the stapes and the long process of the incus to function as a prosthesis when the superstructure of the stapes is missing in the user.

10. The hearing aid device as defined in any one of claim 1, 2, 3, or 4 wherein said vibration generating means includes means for securing said vibration generating means between the handle of the malleus and the footplate of the stapes to bypass the entire upper ossicular chain when the superstructure of the stapes has been damaged and the incus is no longer available for attachment in the user.

11. The hearing aid device as defined in any one of claims 1, 2, 3, or 4 wherein said vibration generating means includes means for securing said vibration generating means to the long process of the incus in the user.

12. The hearing aid device as defined in any one of claims 1, 2, 3, or 4 wherein said vibration generating means includes means for attaching said vibration generating means between the head of the stapes and the handle of the malleus for use with ossicular chain defects producing a gap in the bridge from the tympanic membrane to the inner ear of the user.

13. The hearing aid device as defined in any one of claims 1, 2, 3, or 4 wherein said vibration generating means includes means for attaching said vibration generating means to the head of the stapes for direct vibration of the stapes when a gap is present in the bridge of the bones in the ossicular chain in the middle ear of the user.

14. The hearing aid device as defined in any one of claims 1, 2, 3, or 4 wherein said vibration generating comprises biocompatible material impregnated with rare earth magnetic particles to form a permanent magnet.

* * * * *